United States Patent
Black et al.

(10) Patent No.: US 9,597,168 B2
(45) Date of Patent: Mar. 21, 2017

(54) GUIDANCE ASSEMBLY TIP FOR A LIQUID DROPLET SPRAY TEETH CLEANING APPLIANCE

(75) Inventors: Craig Kortick Black, Bellevue, WA (US); Dainia Edwards, Issaquah, WA (US); Donald Charles Baumgarten, Seattle, WA (US); Ahren Karl Johnson, North Bend, WA (US); Tyler G. Kloster, Snoqualmie, WA (US); Wolter F. Benning, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 730 days.

(21) Appl. No.: 13/512,059

(22) PCT Filed: Nov. 22, 2010

(86) PCT No.: PCT/IB2010/055350
§ 371 (c)(1),
(2), (4) Date: May 25, 2012

(87) PCT Pub. No.: WO2011/077291
PCT Pub. Date: Jun. 30, 2011

(65) Prior Publication Data
US 2012/0270178 A1    Oct. 25, 2012

Related U.S. Application Data

(60) Provisional application No. 61/289,589, filed on Dec. 23, 2009.

(51) Int. Cl.
*A61C 5/04* (2006.01)
*A61C 17/02* (2006.01)

(52) U.S. Cl.
CPC .................... *A61C 17/0202* (2013.01)

(58) Field of Classification Search
CPC .................................... A61C 17/0202
USPC ................. 433/80, 82–89; 601/162–165
See application file for complete search history.

(56) References Cited

U.S. PATENT DOCUMENTS

| | | | | |
|---|---|---|---|---|
| 4,097,995 A * | 7/1978 | Danne et al. | ............. | 433/82 |
| 4,331,422 A * | 5/1982 | Heyman | ............. | 433/125 |
| 4,386,911 A * | 6/1983 | Maloney et al. | ............. | 433/125 |
| 4,672,953 A * | 6/1987 | DiVito | ............. | 601/162 |
| 5,062,413 A * | 11/1991 | Bullard | ............. | 601/162 |
| 5,062,795 A * | 11/1991 | Woog | ............. | 433/80 |

(Continued)

FOREIGN PATENT DOCUMENTS

| | | | |
|---|---|---|---|
| DE | 102006060076 B3 * | 3/2008 | |
| WO | 2007061384 A1 | 5/2007 | |

(Continued)

*Primary Examiner* — Cris L Rodriguez
*Assistant Examiner* — Mirayda A Aponte

(57) ABSTRACT

The guidance assembly is used for precise cleaning of interproximal spaces of teeth. The guidance assembly includes a base portion (30) for contacting the surfaces of teeth and gum region, adjacent the interproximal space, the base portion being approximately 12 mm in diameter to provide stable contact with the teeth and gum region. The guidance assembly also includes a tip portion (28) which extends forward of the base portion and includes an opening (31) through which the droplet spray is directed coincident with the plane of the interproximal space.

17 Claims, 3 Drawing Sheets

(56) References Cited

U.S. PATENT DOCUMENTS

| | | | |
|---|---|---|---|
| 5,653,591 A * | 8/1997 | Loge | 433/118 |
| 5,692,901 A * | 12/1997 | Roth et al. | 433/85 |
| 6,164,967 A * | 12/2000 | Sale et al. | 433/80 |
| 6,626,668 B2 * | 9/2003 | Hubert et al. | 433/80 |
| 6,766,549 B2 * | 7/2004 | Klupt | 15/22.2 |
| 2002/0152565 A1 | 10/2002 | Klupt | |
| 2005/0037316 A1 * | 2/2005 | Sholder | 433/119 |
| 2007/0202459 A1 * | 8/2007 | Boyd et al. | 433/80 |
| 2008/0145814 A1 * | 6/2008 | Pichat et al. | 433/89 |
| 2009/0017423 A1 * | 1/2009 | Gottenbos et al. | 433/216 |
| 2009/0239192 A1 * | 9/2009 | Duineveld et al. | 433/80 |
| 2010/0304327 A1 * | 12/2010 | Grez et al. | 433/88 |
| 2012/0160263 A1 * | 6/2012 | Kotlarchik et al. | 132/322 |
| 2013/0177868 A1 * | 7/2013 | Defenbaugh et al. | 433/80 |

FOREIGN PATENT DOCUMENTS

| | | | |
|---|---|---|---|
| WO | 2008001337 A2 | | 1/2008 |
| WO | WO 2008001337 A2 * | | 1/2008 |
| WO | 2009053892 A1 | | 4/2009 |
| WO | WO 2010140660 A1 * | | 12/2010 |

* cited by examiner

GUIDANCE ASSEMBLY TIP FOR A LIQUID DROPLET SPRAY TEETH CLEANING APPLIANCE

This invention relates generally to liquid droplet spray teeth cleaning appliances, and more particularly concerns a guidance assembly for locating the droplet spray for interproximal cleaning of the teeth.

Liquid droplet spray teeth cleaning appliances are known and are described in several patents and published patent publications. One such patent publication is WO200507034, which is owned by the assignee of the present invention, the contents of which are incorporated herein by reference.

That publication teaches an appliance system for generating liquid, such as water, in the form of droplets and then accelerating those droplets to a desired velocity by a stream of gas, such as air. Other appliance systems use other arrangements to generate and accelerate the liquid droplets. The liquid droplets must have a particular size and velocity to produce effective cleaning of the teeth.

Many of these appliances are designed for home use, which require the user to properly locate the spray nozzle tip of the appliance relative to the teeth, so that the spray reaches the desired area of the teeth. It is a particular challenge for the user to locate the spray properly relative to the interproximal spaces between the teeth. Generally it is more difficult to position the spray tip correctly for the back teeth than for those teeth which are closer to the front. It is difficult for the user to properly locate the spray tip because the spray cannot be directly felt by the user, and for the back teeth cannot be easily seen.

In fact, the spray tip is relatively easy to position incorrectly for the interproximal regions of the teeth. This leads to reduced or poor cleaning in the interproximal areas. It is important for proper cleaning that the spray be precisely aligned and oriented with the interproximal space. An effective guidance tip structure should be configured to provide both correct alignment and orientation of the spray tip to permit the spray to properly enter/engage the interproximal areas.

Accordingly, the guidance member for a liquid droplet spray appliance for cleaning teeth, comprises: a base portion for contacting surfaces of adjacent teeth and gum region, between which teeth is an interproximal space; and a tip portion which extends forward of the base portion, the tip potion terminating at an end which fits into the interproximal space, wherein the tip portion and the base portion are configured so as to provide a reliable, accurate alignment of the tip portion relative to the interproximal space, the top portion extending forward of the base portion and including an opening through which a liquid droplet spray is directed.

Figure 1:
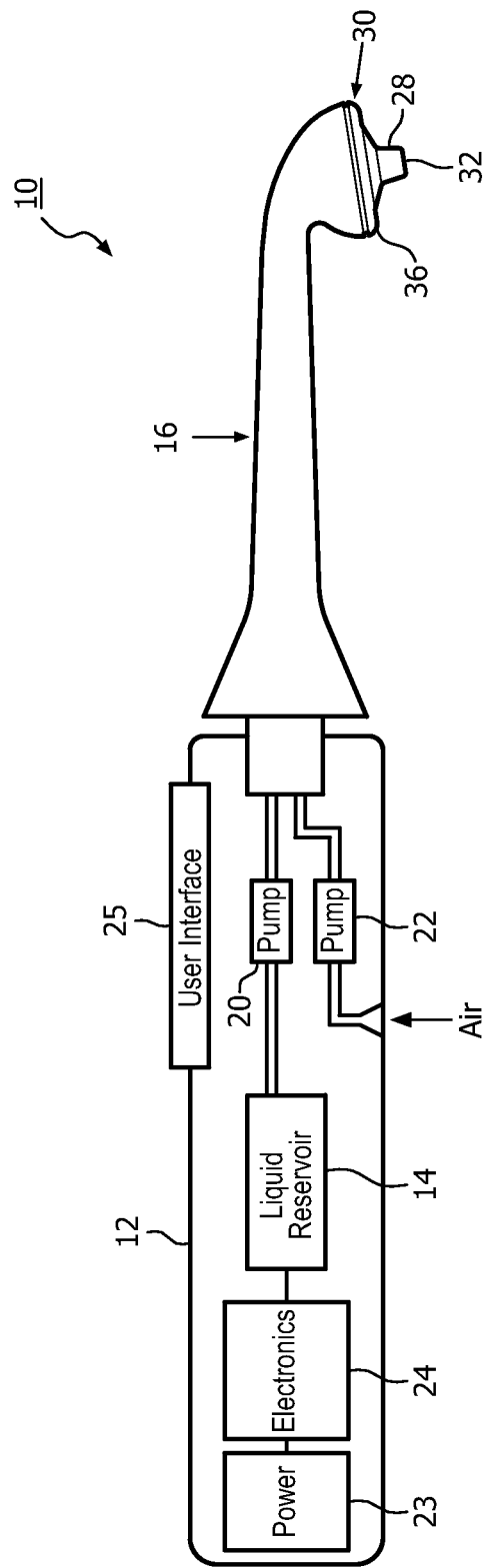
FIG. 1 shows in general a liquid droplet spray teeth cleaning appliance, including the overall nozzle assembly of the appliance.

FIG. 1 shows in general a handheld liquid droplet spray teeth cleaning appliance at 10. The handheld appliance, suitable for home use, includes a handle portion 12 in which is located a reservoir source of liquid 14. In one embodiment, liquid, such as water, from the reservoir and air from the environment are directed to a nozzle and guidance assembly portion 16 of the appliance by separate pumps 20 and 22. The action of the appliance is controlled by a user interface 25. Power is supplied by a power assembly 23, such as a battery, while the appliance is controlled by a microprocessor (electronics) 24. In the nozzle and guidance assembly 16, the gas (air) stream from pump 22 generates droplets from the liquid supplied from reservoir 14 and then accelerates the resulting liquid droplets to a desired exit velocity from a spray tip portion of the appliance to a desired location on the teeth, in particular, the interproximal regions of the teeth.

In one arrangement, the liquid droplets have a size range of 5 microns to 0.5 mm and are accelerated to a velocity of approximately 50 meters per second. Other arrangements, however, with different size droplets and different velocities can be used. For example, the velocity of the liquid droplets can be increased in the range of 10-70 or even up to 200 meters per second.

Figure 2:
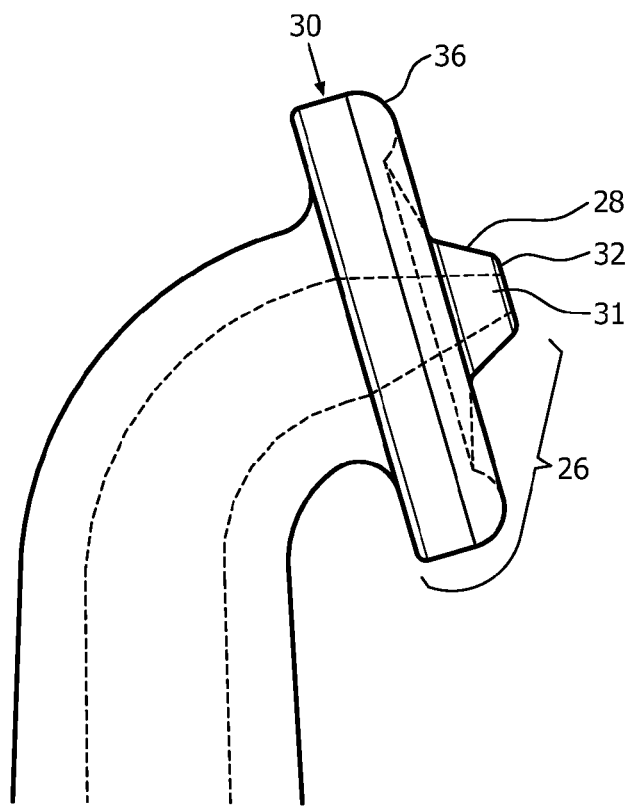
FIG. 2 shows a side elevational view of the spray tip guidance member portion of the nozzle assembly, portions of which are shown in cross section, for clarity of the guidance member.
Figure 3:
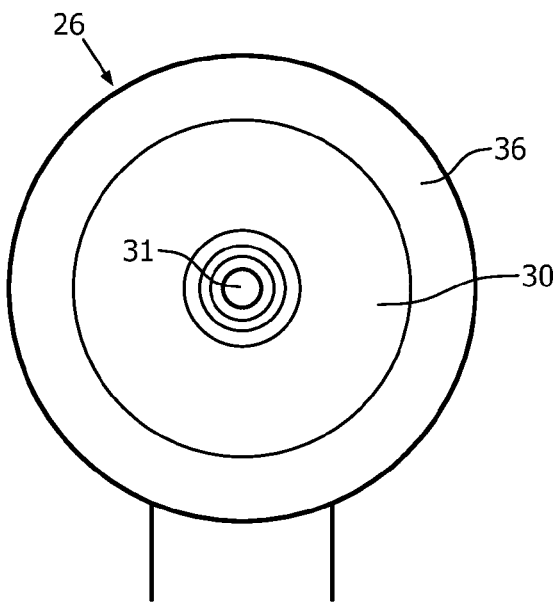
FIG. 3 is a front elevational view of the spray tip guidance member of FIG. 2.
Figure 4:
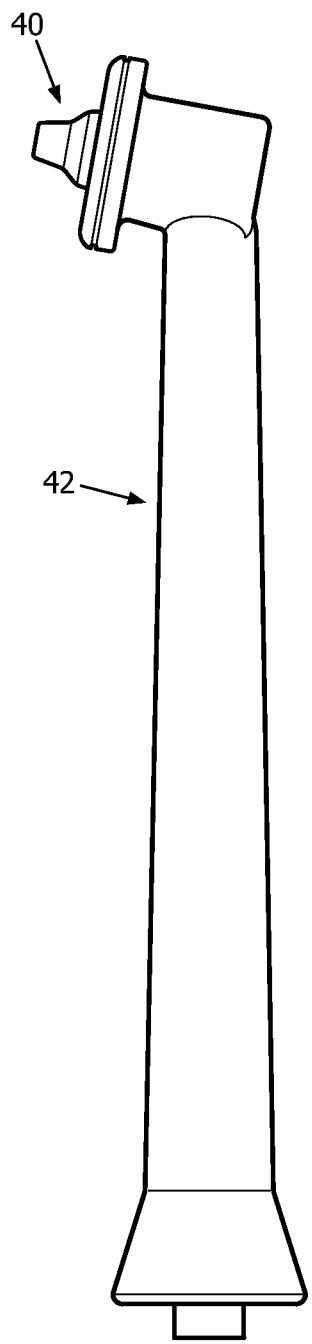
FIG. 4 is a side elevation view of an alternative embodiment.

What is shown and described in FIGS. 2-4 is a nozzle and guidance assembly for the appliance which is configured and arranged to both correctly orient the nozzle tip on the teeth and also to position it so that the spray from the nozzle tip is directed precisely along the interproximal gap between the teeth for effective cleaning thereof. A guidance member portion 26 of nozzle and guidance assembly 16 includes a tip portion 28 and a base portion 30. The tip portion 28 includes a central opening 31 for exit of the liquid droplet spray. The opening 31 is typically 1 mm in diameter, but this could be varied to some extent. The outside diameter of the tip portion 28 at the forward end 32 thereof is approximately 2 mm.

The length of tip portion 28 is typically in the range of 1-3 mm, but is preferably approximately 2.75 mm. The tip portion 28 in the embodiment shown has a slight inward taper from the proximal end thereof, although this is not essential. The configuration of tip portion 28, including the length and diameter thereof are designed to provide good guidance for the droplet spray into the interproximal spaces, particularly for the back teeth, which are more difficult for the user to see, but also for the teeth closer to the front as well. Typically, tip portion 28 is made from hard plastic to provide the desired guidance effect although in some cases, the tip portion could be of softer material.

The base portion 30 of the guidance member portion 26 in the embodiment shown is typically circular, with a diameter in the range of 8-16 mm, with approximately 12 mm being preferred. The thickness (rear to front) of base portion 30 in the embodiment shown is approximately 2 mm. The base portion is typically made of a soft elastomeric material, such as rubber. Around the front perimeter of base portion 30 is a peripheral rim 36 which in the embodiment shown extends approximately 0.5 mm above its point of contact with the remainder of base portion 30, to provide a desired standoff for the guidance member relative to the teeth. The base portion 30 tapers slightly forwardly to where it contacts tip portion 28, as shown in FIG. 2.

It is preferred that the base portion be of relatively soft elastomeric material, while the tip portion be of hard plastic so that the user can distinguish the feel of the tip portion against the teeth relative to the feel of the peripheral rim which also contacts the teeth surfaces. Rim 36 has a curved forward edge to facilitate the comfort of the guidance member for the user as it is positioned in the mouth.

The configuration and size of the base portion 30 is important to provide points of contact as far apart as possible with those teeth adjacent to the interproximal space being cleaned yet still be comfortable within the mouth, as well as providing contact with the adjacent gum region. Such an arrangement provides stability for the guidance member against the teeth and gum region adjacent the interproximal space to be cleaned. It is the base portion 30 of the guidance member which provides the basic alignment of the tip portion 28 relative to the interproximal regions. When base portion 30 is positioned securely on the teeth and the adjacent gum region, the tip portion of the guidance member is precisely aligned with the interproximal space, providing effective cleaning thereof. The guidance tip member thus provides a passive, safe and stable structure for producing the necessary precise alignment of the tip portion on the teeth so that the droplet spray can be directed effectively into the interproximal space.

The tip portion 28 and the base portion 30 have the following important characteristics in the embodiment shown: the opening 21 has a centerline which can be aligned with the plane of the interproximal space; the opening centerline further is parallel to the occlusal plane; the opening centerline is approximately 1.5 mm from the gum at the interproximal site; and the plane of the free end of the tip portion is approximately at most 1.5 mm from the projected tooth contact surface of the 1.0 mm diameter exit opening 21.

Figure 5:
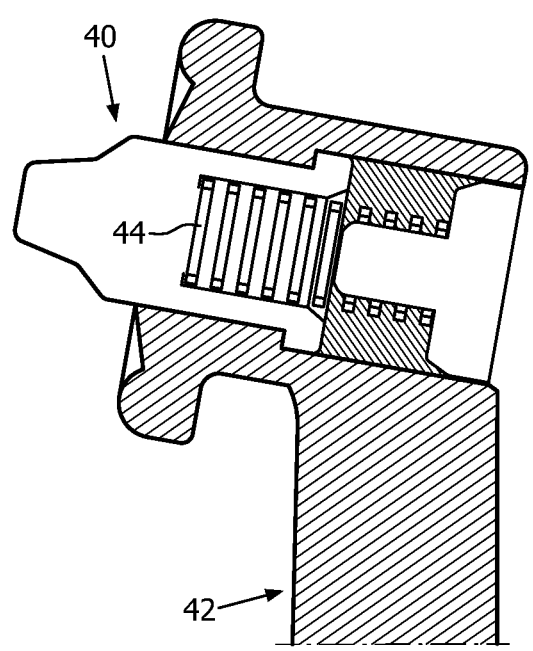
FIG. 5 is a cross-sectional view of the embodiment of FIG. 4.

FIGS. 4 and 5 show an alternative arrangement for the nozzle assembly 42, with an adaptive tip portion 40. Tip portion 40 is mounted on a spring system 44 which provides for a variable extension of the tip portion beyond the base portion.

While the base portion of the guidance member is preferably circular, it could be other shapes, including rectangular or triangular, as long as there is good contact between the base portion and the adjacent teeth and gums of the user. In addition, while the peripheral rim is flat as described and shown herein, with resulting continuous contact with the teeth, it should be understood that the contact surface of the rim might not be continuous, i.e. it could include bumps or bristles or even fingers which produce the contact with the teeth and gum surfaces. It is important, however, that the rim make a good, stable contact with the teeth and gums so as to provide a reliable positioning of the tip portion relative to the interproximal space to be cleaned.

Hence, a guidance tip member for a liquid droplet teeth cleaning appliance has been described which overcomes certain disadvantages of similar prior art appliances and results in precise orientation and alignment of the spray tip portion of the appliance such that the spray is directed precisely into the interproximal gap for effective cleaning of the interproximal regions of the teeth.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. A guidance member for a liquid droplet spray appliance for cleaning teeth, the guidance member positioned at a distal end of a guidance assembly, said guidance assembly defining a longitudinal axis, said guidance member comprising:
a base portion for contacting surfaces of adjacent teeth and gum region, between which teeth is an interproximal space, said base portion positioned at an angle greater than zero degrees and less than 90 degrees with respect to the longitudinal axis of the guidance assembly when said guidance assembly is in a rest position; and
a tip portion which extends forward from a surface of the base portion, the tip portion terminating at an end which is dimensioned and configured to fit into the interproximal space, wherein the tip portion and the base portion are configured so as to provide a reliable, accurate alignment of the tip portion relative to the interproximal space, the tip portion extending forward of the base portion and including an opening through which a liquid droplet spray is directed, wherein due to the position of the base portion, a centerline of the opening of the tip portion, during use of the guidance member, aligns with a plane of the interproximal space.

2. The guidance member of claim 1, wherein the base portion is sufficiently large that it contacts the adjacent teeth and gums when the centerline of the opening is approximately 1.5 mm from the gum region.

3. The guidance member of claim 1, wherein the tip portion comprises a hard plastic material.

4. The guidance member of claim 1, wherein the base portion comprises a soft elastomeric material.

5. The guidance member of claim 1, wherein the base portion includes a peripheral forward rim which extends around the circumference of the base portion, the peripheral rim extending approximately 1 mm forward from its point of contact with the remainder of the base portion.

6. The guidance member of claim 5, wherein the base portion has a diameter of approximately 12 mm.

7. The guidance member of claim 1, wherein the base portion has a diameter within the range of 8-16 mm.

8. The guidance member of claim 1, wherein the opening in the free end of the tip portion is approximately 1 mm in diameter, and wherein the free end has a diameter of approximately 2 mm.

9. The guidance member of claim 1, wherein the base portion other than the peripheral rim is at least 2 mm thick.

10. The guidance member of claim 1, wherein the base portion is approximately circular in configuration.

11. The guidance member of claim 1, wherein the tip portion is centrally positioned with respect to the base portion.

12. The guidance member of claim 1, wherein the peripheral rim of the base portion has a forward contacting surface which is substantially flat and continuous.

13. The guidance member of claim 1, wherein the contacting surface of the peripheral rim includes a plurality of raised elements or protrusions which contact the surface of the adjacent teeth and gum region.

14. The guidance member of claim 1, wherein the tip portion is spring loaded, providing variable positioning of the tip portion relative to the base portion.

15. The guidance member of claim 1, wherein the tip portion tapers outwardly for a distance from the free end thereof in the direction of the base portion.

16. The guidance member of claim 1, wherein the peripheral rim has a rounded forward edge.

17. The guidance member of claim 1, wherein the guidance member is positioned at the distal end of a nozzle and guidance assembly which is removably connected to a handle portion of the appliance.

* * * * *